United States Patent
Guner

(10) Patent No.: US 11,864,517 B2
(45) Date of Patent: *Jan. 9, 2024

(54) INBRED WATERMELON LINE WTL0089

(71) Applicant: Sakata Seed America, Inc., Morgan Hill, CA (US)

(72) Inventor: Nihat Guner, Lehigh Acres, FL (US)

(73) Assignee: Sakata Seed America, Inc., Morgan Hill, CA (US)

( * ) Notice: Subject to any disclaimer, the term of this patent is extended or adjusted under 35 U.S.C. 154(b) by 161 days.

This patent is subject to a terminal disclaimer.

(21) Appl. No.: 17/130,900

(22) Filed: Dec. 22, 2020

(65) Prior Publication Data

US 2022/0192127 A1  Jun. 23, 2022

(51) Int. Cl.
*A01H 5/10* (2018.01)
*A01H 6/34* (2018.01)
*A01H 5/08* (2018.01)
*C12N 15/82* (2006.01)

(52) U.S. Cl.
CPC ............. *A01H 6/342* (2018.05); *A01H 5/10* (2013.01); *C12N 15/8271* (2013.01)

(58) Field of Classification Search
None
See application file for complete search history.

(56) References Cited

U.S. PATENT DOCUMENTS 9,848,548 B1 * 12/2017 Bernier ............. C12N 15/8241

* cited by examiner

*Primary Examiner* — Jason Deveau Rosen
(74) *Attorney, Agent, or Firm* — Weatherly IP Solutions, LLC; James M. Weatherly

(57) ABSTRACT

One embodiment relates to seed and plants of inbred watermelon line WTL0089. Another embodiment relates to the plants, seeds and tissue cultures of inbred watermelon line WTL0089, and to methods for producing a watermelon plant produced by crossing such plants with themselves, with another watermelon plant, such as a plant of another genotype, or with vegetatively propagating said plant. Another embodiment further relates to seeds and plants produced by such crossing. Further embodiments relate to parts of such plants, including the fruit and gametes of such plants.

26 Claims, No Drawings

INBRED WATERMELON LINE WTL0089

BACKGROUND

*Citrullus lanatus*, watermelon, is a plant which is included in the family Cucurbitaceae. Watermelon is an economically important crop and is used in a number of consumer and commodity products.

The foregoing examples of the related art and limitations related therewith are intended to be illustrative and not exclusive. Other limitations of the related art will become apparent to those of skill in the art upon a reading of the specification.

SUMMARY

It is to be understood that the embodiments include a variety of different versions or embodiments, and this summary is not meant to be limiting or all-inclusive. This summary provides some general descriptions of some of the embodiments, but may also include some more specific descriptions of other embodiments.

The embodiments recited herein relates to a novel and distinct inbred watermelon, *C. lanatus*, line designated WTL0089, and to the seeds, plant parts, and tissue culture produced by that inbred watermelon line. The embodiments further relate to fresh food and food products produced from inbred watermelon line WTL0089, such as, but not limited to products such as watermelon fruit, powders, juices, sweetener, colorings, watermelon pulp, watermelon shreds, raffinate and betaine. All publications cited in this application are herein incorporated by reference.

An embodiment provides an inbred watermelon line designated WTL0089. Another embodiment relates to the seeds of inbred watermelon line WTL0089, to the plants of inbred watermelon line WTL0089 and to methods for producing a watermelon plant produced by crossing inbred watermelon line WTL0089 with itself or another inbred watermelon line, and the creation of variants by mutagenesis or transformation of inbred watermelon line WTL0089.

Any such methods using inbred watermelon line WTL0089 are a further embodiment: selfing, backcrosses, hybrid production, crosses to populations, and the like. All plants produced using inbred watermelon line WTL0089 as at least one parent are within the scope of the embodiments. Advantageously, inbred watermelon line WTL0089 could be used in crosses with other, different watermelon plants to produce first generation ($F_1$) watermelon hybrid seeds and plants with superior characteristics.

Another embodiment provides for single or multiple gene converted plants of inbred watermelon line WTL0089. The transferred gene(s) may be a dominant or recessive allele. The transferred gene(s) may confer such traits as herbicide tolerance, insect tolerance, tolerance for bacterial, fungal, or viral disease, male fertility, male sterility, enhanced nutritional quality, environmental stress tolerance, modified carbohydrate metabolism, modified yield, modified glycoalkaloid content, and industrial usage. The gene may be a naturally occurring watermelon gene or a transgene introduced through genetic engineering techniques.

Another embodiment provides for regenerable cells for use in tissue culture of inbred watermelon line WTL0089. The tissue culture may be capable of regenerating plants having all the physiological and morphological characteristics of the foregoing watermelon plant, and of regenerating plants having substantially the same genotype as the foregoing watermelon plant. The regenerable cells in such tissue cultures may be embryos, protoplasts, meristematic cells, callus, pollen, leaves, ovules, anthers, cotyledons, hypocotyl, pistils, roots, root tips, flowers, seeds, plant, petiole, or stems. Still a further embodiment provides for watermelon plants regenerated from the tissue cultures of inbred watermelon line WTL0089.

Another embodiment relates to a method of vegetatively propagating inbred watermelon line WTL0089 comprising the steps of: (a) collecting tissue capable of being propagated from the plant; (b) cultivating said tissue to obtain proliferated shoots; and (c) rooting said proliferated shoots to obtain rooted plantlets.

Another embodiment provides for a method for producing a hybrid seed of hybrid line XWT8028 from inbred watermelon line WTL0089 comprising the steps of: (a) crossing female inbred line WTL0089 with the male inbred line WDL0090, and (b) allowing seed of hybrid watermelon XWT8028 to form.

Another embodiment provides for a method for producing a hybrid seed from inbred watermelon line WTL0089 comprising the steps of: (a) crossing the watermelon plant with another inbred watermelon plant, and (b) allowing seed of a hybrid watermelon plant to form.

Another embodiment provides for a method for producing a seed of a watermelon plant derived from inbred watermelon line WTL0089 comprising the steps of: (a) crossing the watermelon plant with itself or a second watermelon plant, and (b) allowing seed of an inbred WTL0089-derived watermelon plant to form.

Further embodiments provide for a method of producing food or feed comprising: (a) obtaining a plant of inbred watermelon line WTL0089, wherein the plant has been cultivated to maturity, and (b) collecting at least one watermelon from the plant.

In another embodiment, the first step in "crossing" comprises planting seeds of a first and second parent watermelon plant, often in proximity so that pollination will occur for example, mediated by insect vectors. Alternatively, pollen can be transferred manually. Where the plant is self-pollinated, pollination may occur without the need for direct human intervention other than plant cultivation. A second step may comprise cultivating or growing the seeds of first and second parent watermelon plants into plants that bear flowers. A third step may comprise preventing self-pollination of the plants, such as by emasculating the flowers (i.e., killing or removing the pollen). A fourth step for a hybrid cross may comprise cross-pollination between the first and second parent watermelon plants. Yet another step comprises harvesting the seeds from at least one of the parent watermelon plants. The harvested seed can be grown to produce a watermelon plant or hybrid tomato plant.

Another embodiment provides for a method for developing a watermelon plant in a plant breeding program, comprising applying plant breeding techniques to the plant, or plant part thereof, to inbred watermelon line WTL0089, comprising crossing, recurrent selection, mutation breeding, wherein said mutation breeding selects for a mutation that is spontaneous or artificially induced, backcrossing, pedigree breeding, marker enhanced selection, haploid/double haploid production, or transformation to inbred watermelon line WTL0089, or its parts, wherein application of said techniques results in development of a watermelon plant.

Another embodiment provides for a method of introducing a mutation into the genome of inbred watermelon line WTL0089, said method comprising mutagenesis of the plant, or plant part thereof, of watermelon plant WTL0089, wherein said mutagenesis is selected from the group consisting of temperature, long-term seed storage, tissue culture conditions, ionizing radiation, chemical mutagens, or targeting induced local lesions in genomes, and wherein the resulting plant comprises at least one genome mutation.

Another embodiment provides for a method of editing the genome of watermelon plant WTL0089, said method comprising editing the genome of the plant, or plant part thereof, of watermelon plant WTL0089, wherein said method is selected from the group comprising zinc finger nucleases, transcription activator-like effector nucleases (TALENs), engineered homing endonucleases/meganucleases, and the clustered regularly interspaced short palindromic repeat (CRISPR)-associated protein9 (Cas9) system.

The watermelon seed of WTL0089 may be provided as an essentially homogeneous population of seed of inbred watermelon line WTL0089. Essentially homogeneous populations of seed are generally free from substantial numbers of other seed.

Another embodiment provides for the genetic complement of inbred watermelon line WTL0089. The phrase "genetic complement" is used to refer to the aggregate of nucleotide sequences, the expression of which sequences defines the phenotype of, in the present case, a watermelon plant, or a cell or tissue of that plant. A genetic complement thus represents the genetic makeup of a cell, tissue or plant, and a hybrid genetic complement represents the genetic make-up of a hybrid cell, tissue or plant. Thus, another embodiment provides for watermelon plant cells that have a genetic complement in accordance with the watermelon plant cells disclosed herein, and seeds and plants containing such cells.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

Various embodiments are set forth in the Detailed Description as provided herein and as embodied by the claims. It should be understood, however, that this Summary does not contain all of the aspects and embodiments, is not meant to be limiting or restrictive in any manner, and that embodiment(s) as disclosed herein is/are understood by those of ordinary skill in the art to encompass obvious improvements and modifications thereto.

In addition to the exemplary aspects and embodiments described above, further aspects and embodiments will become apparent by study of the following descriptions.

DEFINITIONS

In the description and tables herein, a number of terms are used. In order to provide a clear and consistent understanding of the specification and claims, including the scope to be given such terms, the following definitions are provided:

Cotyledon. A cotyledon is a type of seed leaf. The cotyledon contains the food storage tissues of the seed.

Embryo. The embryo is the small plant contained within a mature seed.

Gene. Gene refers to a segment of nucleic acid. A gene can be introduced into a genome of a species, whether from a different species or from the same species, using transformation or various breeding methods.

Hypocotyl. A hypocotyl is the portion of an embryo or seedling between the cotyledons and the root. Therefore, it can be considered a transition zone between shoot and root.

Locus. Locus or loci (plural) refers to a position in the genome for a gene, SNP, mutation, etc.

Plant Part(s). Plant part(s) (or a watermelon plant, or a part thereof) includes but is not limited to, regenerable cells in such tissue cultures may be embryos, taproot, protoplasts, cells, meristematic cells, callus, pollen, leaves, ovules, embryos, anthers, cotyledons, hypocotyl, pistils, roots, rootstock, root tips, scion, stock, taproots, flowers, fruit, seeds, shoot, plant, petiole, or stems.

Progeny. Progeny includes an $F_1$ watermelon plant produced from the cross of two watermelon plants where at least one plant includes inbred watermelon line WTL0089 and progeny further includes, but is not limited to, subsequent $F_2$, $F_3$, $F_4$, $F_5$, $F_6$, $F_7$, $F_8$, $F_9$, and $F_{10}$ generational crosses.

Rootstock. Rootstock or stock refers to the plant selected for its roots, in particular for the resistance of the roots to diseases or stress (e.g., heat, cold, salinity etc.). Normally the quality of the fruit of the plant providing the rootstock is less important.

Scion. Scion refers to a part of the plant attached to the rootstock. This plant is selected for its stems, leaves, flowers, or fruits. The scion contains the desired genes to be duplicated in future production by the stock/scion plant and may produce the desired tomato fruit.

Stock/scion. Stock/scion or grafted plant refers to a tomato plant comprising a rootstock from one plant grafted to a scion from another plant.

DETAILED DESCRIPTION

Inbred watermelon lines WTL0088, WTL0089, WDL0090 and WTL0091 originated from a private breeding program in the state of Florida. Inbred watermelon line WTL0088, WTL0089, and WTL0091 are female inbred watermelon lines and inbred watermelon line WDL0090 is a male inbred watermelon line.

Inbred watermelon lines WTL0088, WTL0089, WDL0090 and WTL0091 have shown uniformity and stability, as described in the following variety description information. Inbred watermelon lines WTL0088, WTL0089, WDL0090 and WTL0091 were tested for uniformity and stability a sufficient number of generations with careful attention to uniformity of plant type and has been increased with continued observation for uniformity.

Inbred watermelon lines WTL0088, WTL0089, WDL0090 and WTL0091 have the following morphologic and other characteristics based primarily on data collected in Woodland, California, Aug. 16-17, 2020 as shown in Table 1.

TABLE 1

VARIETY DESCRIPTION INFORMATION

| Characteristic | WTL0088 | WTL0091 | WTL0089 | WDL0090 |
|---|---|---|---|---|
| Type | Female inbred | Female inbred | Female inbred | Male inbred |
| Ploidy | Tetraploid | Tetrapioid | Tetraploid | Diploid |
| Maturity | Average | Average | Average | Average |
| Plant vigor | Excellent | Excellent | Excellent | Very good |
| Leaf type | Lobed | Lobed | Lobed | Non-lobed |
| Sex expression | Monecious | Monoecious | Monoecious | Monoecious |
| Stem | | | | |
| Stem shape (cross section) | Circular | Circular | Circular | Circular |
| Diameter at second node | 6.0 mm | 7.0 mm | 7.0 mm | 6.0 mm |
| Stem surface | Pubescent | Pubescent | Pubescent | Pubescent |
| Vine length at harvest | 225 cm | 215 cm | 228 cm | 210 cm |
| Number of internodes at harvest | 34 | 26 | 29 | 22 |
| Ratio of vine length to internodes | 6.62 | 8.27 | 7.86 | 9.55 |
| Leaf | | | | |
| Leaf shape | Obovate | Obovate | Obovate | Obovate |
| Leaf lobes | Lobed | Lobed | Lobed | Lobed |
| Leaf length | 15.0 cm | 12.3 cm | 15.8 cm | 13.4 cm |
| Leaf width | 18.4 cm | 14.4 cm | 16.1 cm | 9.8 cm |
| Leaf size (length:width) | 0.82 | 0.85 | 0.98 | 1.37 |
| Dorsal surface pubescence | Pubescent | Slightly pubescent | Pubescent | Very Slight Pubescence |
| Ventral surface pubescence | Pubescent | Pubescent | Pubescent | Very Slight Pubescence |
| Leaf color (upper) | RHS 147B | RHS NN137B | RHS NN137B | RHS NN137B |
| Leaf color (lower) | Closest to RHS 147C | Closest to but lighter than RHS 147B | Closest to but lighter than RHS 147B | Closest to RHS 147B |
| Flower | | | | |
| Diameter of staminate | 3.1 cm | 2.9 cm | 3.3 cm | 3.3 cm |
| Diameter of pistilate | 3.0 cm | 2.8 cm | 3.1 cm | 3.0 cm |
| Flower color | RHS 5B | RHS 5A | RHS 5A | RHS 6A |
| Fruit | | | | |
| Fruit shape | Round | Round | Round | Oval |
| Length | 25.0 cm | 26.8 cm | 27.4 | 46 |
| Diameter at midsection | 26.8 cm | 29.0 cm | 26 | 22.8 |
| Average weight | 14.45 lbs | 23.6 lbs | 20.67 lbs | 28 lbs |
| Fruit surface | Smooth | Smooth | Smooth | Smooth |
| Rind pattern | Crimson sweet | Crimson sweet | Crimson Sweet | All sweet |
| Rind background color | Medium dark green | Medium dark green | Medium dark green | Light green |
| Rind primary color | Closest to but darker than RHS 139A | Closest to but darker then RHS 139A | Closest to but darker than 139A | 139A |
| Rind stripe color | Dark green | Dark green | Dark Green | Medium Dark Green |
| Rind secondary color | RHS 143A | RHS 143A | 143A | 144A |
| Rind tertiary color | 145B | 145C | 145C | 145B |
| Rind stripe width | Medium | Medium | Medium | Wide |
| Rind texture | Tough | Tough | Tough | Tough |
| Rind thickness at blossom end | 21.0 mm | 20.0 mm | 15.0 mm | 8.0 mm |
| Rind thickness - sides | 17.0 mm | 15.0 mm | 12.0 mm | 13.0 mm |
| Internal/Flesh | | | | |
| Flesh texture | Crisp | Crisp | Crisp | Crisp |
| Flesh coarseness | Fine-little fiber | Fine-little fiber | Fine-little fiber | Fine-little fiber |
| Flesh color | RHS 35A with RHS 42B | RHS 42B | RHS 35A with RHS 42B | RHS 42B |
| Flesh color | Deep red | Deep red | Deep Red | Bright Red |
| Seed | | | | |
| Seed color | Tipped, closest to RHS 165B with RHS 200A at tip | Mottled Black; RHS 200A and RHS 165A | Striped; RHS 164A with RHS 200B | RHS 203A edges with RHS 164A in the middle |
| Seed size | Medium | Medium | Medium | Small |
| Seed length | 10.0 mm | 10.0 mm | 11.0 mm | 8.0 mm |
| Seed width | 7.5 mm | 7.5 mm | 7.0 mm | 5.0 mm |
| Seed thickness | 2.5 mm | 3.0 mm | 2.5 mm | 2.0 mm |
| Seed yield per fruit | 56 | 200 | 140 | 588 |
| Disease resistance | | | | |
| Disease resistance | *Fusarium oxysporum* f. sp. *niveum* (FON) race 1 | *Fusarium oxysporum* f. sp. *niveum* (FON) race 1 | *Fusarium oxysporum* f. sp. *niveum* (FON) race 1 | *Fusarium oxysporum* f. sp. *niveum* (FON) race 1 and *Colletotrichum orbiculare* |

Table 2 below provides a comparison of penetrometer or flesh firmness of inbred watermelon lines WTL0088, WTL0089, WDL0090 and WTL0091. A penetrometer is a device that is used to determine the firmness of the flesh of watermelon by punching holes in the flesh of the watermelon. A standard penetrometer with an 11 mm wide probe was used. Ten fruit were cut in half length wise and a penetrometer was used to puncture the flesh in a cross shape on the center of each watermelon half in the same location and the same speed with ten readings on each inbred. Table 2 below shows the results of the ten reading on each inbred as well as the statistical analysis of the data.

TABLE 2

Watermelon Firmness Measured by a Penetrometer

|    | WTL0088 | WTL0091 | WTL0089 | WDL0090 |
|---|---|---|---|---|
| 1 | 3.4 | 5.1 | 4.4 | 3.6 |
| 2 | 2.8 | 4 | 3.5 | 4 |
| 3 | 4.5 | 4 | 2.8 | 4.3 |
| 4 | 5.5 | 5 | 4.1 | 3.3 |
| 5 | 4.6 | 4.3 | 2.7 | 2.2 |
| 6 | 2.3 | 2.8 | 2.7 | 2.2 |
| 7 | 3.3 | 3.1 | 2.6 | 2.8 |
| 8 | 2.4 | 2.5 | 3 | 2.4 |
| 9 | 2.7 | 3.8 | 3.5 | 3 |
| 10 | 2.2 | 3.8 | 4.4 | 5 |
| Mean | 3.18 | 3.84 | 3.37 | 3.28 |
| Standard error | 0.19 | 0.27 | 0.23 | 0.30 |
| Median | 3.20 | 3.90 | 3.25 | 3.15 |
| Mode | 3.20 | 4.00 | 4.40 | 2.20 |
| Standard deviation | 0.61 | 0.86 | 0.72 | 0.94 |
| Sample variance | 0.37 | 0.74 | 0.52 | 0.89 |

Inbred watermelon lines WTL0088, WTL0089, WDL0090 and WTL0091 as well as the hybrid lines XWT8009, WT8018, and XWT8028 described below may also be grown for use as rootstocks (stocks) or scions. Typically, different types of watermelon are grafted to enhance disease resistance, which is usually conferred by the rootstock, while retaining the horticultural qualities usually conferred by the scion. It is not uncommon for grafting to occur between cultivated watermelon varieties and related watermelon species. Methods of grafting and vegetative propagation are well-known in the art.

In another aspect, the disclosure provides to a plant comprising a rootstock or scion of WTL0088, WTL0089, WDL0090 and WTL0091 as well as the hybrid lines XWT8009, WT8018, and XWT8028.

One aspect of the current disclosure concerns methods for hybrid watermelon seed produced from breeding with inbred line WTL0088 as a parental line. In one example, inbred line WTL0088 is used as a female line and crossed with the male inbred watermelon WDL0090 to produce the hybrid XWT8009 (described below in Table 3). Alternatively, in other embodiments, inbred line WTL0088 may be crossed with another inbred line to produce additional hybrid lines. Additionally, inbred line WTL0088, hybrid line XWT8009 or inbred line WDL0090 may be may be crossed with itself or with any second plant. Such methods can be used for propagation of hybrid XWT8009, and/or the watermelon lines WTL0088 and WDL0090, or can be used to produce plants that are derived from hybrid XWT8009, and/or the watermelon lines WTL0088 and WDL0090. Plants derived from hybrid XWT8009, and/or the watermelon lines WTL0088 and WDL0090 may be used, in certain embodiments, for the development of new watermelon varieties.

Another aspect of the current disclosure concerns methods for hybrid watermelon seed produced from breeding with inbred line WTL0089 as a parental line. In one example, inbred line WTL0089 is used as a female line and crossed with the male inbred watermelon WDL0090 to produce the hybrid XWT8028 (described below in Table 3). Alternatively, in other embodiments, inbred line WTL0089 may be crossed with another inbred line to produce additional hybrid lines. Additionally, inbred line WTL0089, hybrid line XWT8028 or inbred line WDL0090 may be may be crossed with itself or with any second plant. Such methods can be used for propagation of hybrid XWT8028, and/or the watermelon lines WTL0089 and WDL0090, or can be used to produce plants that are derived from hybrid XWT8028, and/or the watermelon lines WTL0089 and WDL0090. Plants derived from hybrid XWT8028, and/or the watermelon lines WTL0089 and WDL0090 may be used, in certain embodiments, for the development of new watermelon varieties.

One aspect of the current disclosure concerns methods for hybrid watermelon seed produced from breeding with inbred line WTL0091 as a parental line. In one example, inbred line WTL0091 is used as a female line and crossed with the male inbred watermelon WDL0090 to produce the hybrid WT8018 (described below in Table 3). Alternatively, in other embodiments, inbred line WTL0091 may be crossed with another inbred line to produce additional hybrid lines. Additionally, inbred line WTL0091, hybrid line WT8018 or inbred line WDL0090 may be may be crossed with itself or with any second plant. Such methods can be used for propagation of hybrid XWT8018, and/or the watermelon lines WTL0091 and WDL0090, or can be used to produce plants that are derived from hybrid WT8018, and/or the watermelon lines WTL0091 and WDL0090. Plants derived from hybrid WT8018, and/or the watermelon lines WTL0091 and WDL0090 may be used, in certain embodiments, for the development of new watermelon varieties.

Hybrid watermelon lines XWT8009, WT8018, and XWT8028, as described above, originated from a private breeding program in the state of Florida. Hybrid watermelon lines XWT8009, WT8018, and XWT8028 have the following morphologic and other characteristics based primarily on data collected in Woodland, California 2020 as shown in Table 3.

Table 4 provide a comparison of hybrid watermelon lines XWT8009, WT8018, and XWT8028 with the commercial hybrid triploid watermelon lines Charismatic, Troubador, Traveler, Fascination, Unbridled, Exclamation, Maxima, and Captivation. The comparison trial was conducted in Woodland, California in 2019.

TABLE 3

| HYBRID DESCRIPTION INFORMATION | | | |
|---|---|---|---|
| Characteristic | XWT8009 | XWT8018 | XWT8028 |
| | Mature Fruit | | |
| Fruit Shape | Oval | Oval | Oval |
| cm long | 30.7 cm | 32.5 cm | 32.5 cm |
| cm diameter at midsection | 26.6 cm | 26.8 cm | 24.6 cm |
| lbs avg. weight | 17.93 lbs | 20.33 lbs | 22.87 lbs |

TABLE 3-continued

HYBRID DESCRIPTION INFORMATION

| Characteristic | XWT8009 | XWT8018 | XWT8028 |
|---|---|---|---|
| Index (length/diameter)*10) | 11.54 | 12.13 | 13.21 |
| Fruit Surface | Smooth | Smooth | Smooth |
| Skin Color Pattern | Stripe | Stripe | Stripe |
| Primary color | Closest to but darker than 139A (Dark Yellowish Green) | Closest to but darker than 139A (Dark Yellowish Green) | Closest to but darker than 139A |
| Secondary Color | 143A (Strong Yellow Green) | 144A | Closest to but darker than 143A (Strong Yellow Green) |
| Tertiary Color | 145C | Closest to 145B | Closest to 145B |
| Rind | | | |
| Rind Texture | Tough | Tough | Tough |
| Thickness at blossom end | 12 mm | 16 mm | 10 mm |
| Thickness sides | 11 mm | 11 mm | 14.5 mm 18 mm on one side, 11 mm on other side |
| Flesh | | | |
| Flesh Texture | Crisp | Crisp | Crisp |
| Flesh Coarseness | Fine-Little Fiber | Fine-Little Fiber | Fine-Little Fiber |
| Flesh Color | 42A with 39A | 42B with 42C | Between 42A and 42B |
| Disease Resistance | Fo Race 1 | Fo Race 1 | Fo Race 1 |
| Penetrometer | 2.93 | 4.73 | 3.00 |

TABLE 4

COMPARISON OF HYBRIDS WITH COMMERICAL TRIPLOID LINES

| Characteristic | XWT8009 | XWT8018 | XWT8028 | Charismatic | Troubador | Traveler |
|---|---|---|---|---|---|---|
| General Fruit Type | Oblong | Oblong | Oblong | Oblong | Oblong | Oblong |
| Ploidy | Triploid | Triploid | Triploid | Triploid | Triploid | Triploid |
| Stem | | | | | | |
| Stem Shape (in Cross section) | Circular | Circular | Circular | Circular | Circular | Circular |
| mm diameter at second node | 5 | 7 | 7 | 6 | 5 | 7 |
| Stem Surface | Bristled | Pubescent | Pubescent | Pubescent | Pubescent | Pubescent |
| cm vine length at last harvest | 330 | 345 | 277 | 285 | 137 | 148 |
| # of internodes at last harvest | 36 | 35 | 31 | 34 | 11 | 26 |
| Ratio - Vine length: # Of Internodes | 9.17 | 9.86 | 8.94 | 8.38 | 12.45 | 5.69 |
| Leaf | | | | | | |
| cm leaf length | 13.47 | 12.4 | 13.73 | 14.23 | 12.77 | 15.7 |
| cm leaf width | 12.87 | 11.8 | 13.73 | 11.37 | 10.57 | 13.43 |
| Leaf size (length:Width) | 1.05 | 1.05 | 1.00 | 1.25 | 1.21 | 1.17 |
| Leaf color | Upper: RHS 147A (Moderate Olive Green) Lower: RHS 147C (Moderate Yellow Green) | RHS 147B (Moderate Yellow Green) | RHS NN137C (Greyish Olive Green) | Upper: NN137B (Greyish Olive Green) Lower: 191A (Greyish Yellow Green) | RHS 147A (Moderate Olive Green) | RHS N148A (Moderate Yellow Green) |
| Flower | | | | | | |
| cm diameter Staminate | 3.5 | 2.8 | 2.7 | 3.6 | 4.1 | 3.3 |
| cm diameter Pistilate | 3.6 | 3.8 | 2.5 | 3.8 | 3.8 | 2.5 |
| Flower Color | RHS 8A (Brilliant Yellow) | RHS 9B (Vivid Yellow) | RHS 6B (Brilliant Greenish Yellow) | RHS 4B (Light Greenish Yellow) | RHS 3C (Light Greenish Yellow) | RHS 4B (Light Greenish Yellow) |
| Mature Fruit | | | | | | |
| Fruit Shape | Oval | Oval | Oval | Oval | Oval | Oval |
| cm long | 27 | 30 | 28 | 27 | 23 | 24 |
| cm diameter at midsection | 22 | 22 | 23 | 25 | 20 | 22 |

TABLE 4-continued

COMPARISON OF HYBRIDS WITH COMMERICAL TRIPLOID LINES

| | | | | | | |
|---|---|---|---|---|---|---|
| lbs avg. weight | 18-20 | 22-24 | 20-22 | 16-20 | 14-17 | 15-20 |
| Index (length/diameter) *10) | 12.27 | 13.64 | 12.17 | 10.80 | 11.50 | 10.91 |
| Primary color | Closest to but darker than RHS 139A (Dark Yellowish Green) | Lighter than RHS 139A | Closest to but much darker than RHS 139A | Between RHS 146B and RHS 146A | RHS 139A | Closest to but lighter than RHS 139A |
| Secondary Color | RHS 143A (Strong Yellow Green) | RHS 144C (Strong Yellow Green) | RHS 143A (Strong Yellow Green) | RHS N144C | RHS 144A (Strong Yellow Green) | RHS 138A |
| Tertiary Color | RHS 145C | RHS 145D | RHS 145C | RHS 194C | RHS 144D | RHS 147D |

Rind

| | | | | | | |
|---|---|---|---|---|---|---|
| Rind Texture | Tough | Tough | Tough | Tough | Tough | Tough |
| mm thickness at blossom end | 22 | 17 | 16 | 17 | 25 | 35 |
| mm thickness sides | 14 | 11 | 12 | 12 | 17 | 15 |

Flesh

| | | | | | | |
|---|---|---|---|---|---|---|
| Flesh Texture | Crisp | Crisp | Crisp | Crisp | Crisp | Crisp |
| Flesh Coarseness | Fine-Little Fiber | Fine-Little Fiber | Fine-Little Fiber | Fine-Little Fiber | Fine-Little Fiber | Fine-Little Fiber |
| Flesh Color | 44A | Closest to but lighter than 42A | 44C | Between 42C and 42D | 42A | 45B |
| Disease Resistance | Fo Race 1 | Fo Race 1 | Fo Race 1 | | | HR: Co (1) |
| Penetrometer | 4.05 | 3.68 | 3.78 | 3.53 | 4.18 | 3.43 |

| Characteristic | Fascination | Unbridled | Exclamation | Maxima | Captivation |
|---|---|---|---|---|---|
| General Fruit Type | Oblong | Oblong | Oblong | Oblong | Oblong |
| Ploidy | Triploid | Triploid | Triploid | Triploid | Triploid |

Stem

| | | | | | |
|---|---|---|---|---|---|
| Stem Shape (in Cross section) | Circular | Circular | Circular | Circular | Circular |
| mm diameter at second node | 7 | 5 | 7 | 7 | 8 |
| Stem Surface | Bristled | Pubescent | Pubescent | Bristled | Bristled |
| cm vine length at last harvest | 160 | 92 | 150 | 220 | 140 |
| # of internodes at last harvest | 22 | 16 | 15 | 22 | 18 |
| Ratio - Vine length: # Of Internodes | 7.27 | 5.75 | 10.00 | 10.00 | 7.78 |

Leaf

| | | | | | |
|---|---|---|---|---|---|
| cm leaf length | 16.87 | 15.53 | 13.33 | 12.07 | 14.7 |
| cm leaf width | 16.33 | 14.33 | 13.5 | 11.8 | 12.8 |
| Leaf size (length:Width) | 1.03 | 1.08 | 0.99 | 1.02 | 1.15 |
| Leaf color | RHS N148A (Moderate Yellow Green) | RHS NN137B (Greyish Olive Green) | RHS 137C (Moderate Yellow Green) | RHS NN137A (Greyish Olive Green) | RHS 147A (Moderate Olive Green) |

Flower

| | | | | | |
|---|---|---|---|---|---|
| cm diameter Staminate | 2 | 3.9 | 2.5 | 3 | 4 |
| cm diameter Pistilate | 2 | 3.6 | 2.8 | 3 | 3.5 |
| Flower Color | RHS 8B (Light Greenish Yellow) | RHS 5B (Brilliant Greenish Yellow) | RHS 6B (Brilliant Greenish Yellow) | RHS 3A (Brilliant Greenish Yellow) | RHS 4A (Brilliant Greenish Yellow) |

Mature Fruit

| | | | | | |
|---|---|---|---|---|---|
| Fruit Shape | Oval | Cylindrical | Cylindrical | Cylindrical | Cylindrical |
| cm long | 28 | 25 | 25 | 26 | 25 |
| cm diameter at midsection | 23 | 22 | 22 | 24 | 21 |
| lbs avg. weight | 16-20 | 18-22 | 17-21 | 19-22 | 14-17 |
| Index (length/diameter) *10) | 12.17 | 11.36 | 11.36 | 10.83 | 11.90 |
| Primary color | RHS 137A (Moderate Olive Green) | RHS 137B | RHS 137B | RHS 139A | RHS 137A |
| Secondary Color | RHS 145A | RHS 144A | RHS 144C (Strong Yellow Green) | RHS 143A | RHS 143C (Strong Yellow Green) |

TABLE 4-continued

| COMPARISON OF HYBRIDS WITH COMMERICAL TRIPLOID LINES | | | | | |
|---|---|---|---|---|---|
| Tertiary Color | RHS 149D | RHS 147D | RHS 145D | RHS 145B | RHS 145D (Light Yellow Green) |
| Rind | | | | | |
| Rind Texture | Tough | Tough | Tough | Tough | Tough |
| mm thickness at blossom end | 16 | 28 | 16 | 30 | 17 |
| mm thickness sides | 14 | 15 | 12 | 15 | 15 |
| Flesh | | | | | |
| Flesh Texture | Crisp | Crisp | Crisp | Crisp | Crisp |
| Flesh Coarseness | Fine-Little Fiber | Fine-Little Fiber | Fine-Little Fiber | Fine-Little Fiber | Fine-Little Fiber |
| Flesh Color | Slightly darker than 42D | Closest to RHS 42C (Strong Reddish Orange) | 42A | Closest to but lighter than 42A | 42B |
| Disease Resistance | IR: Co (1) IR: Fo (1) | | IR: Co (1) IR: Fo (1) | | IR: Co (1) IR: Fo (1) |
| Penetrometer | 3.43 | 3.00 | 3.82 | 3.75 | 3.85 |

Breeding with Inbred Watermelon Line WTL0088, WTL0089, WDL0090 or WTL0091

The complexity of inheritance influences choice of the breeding method. Backcross breeding is used to transfer one or a few favorable genes for a highly heritable trait into a desirable variety. This approach has been used extensively for breeding disease-resistant varieties. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Promising advanced breeding lines are thoroughly tested and compared to appropriate standards in environments representative of the commercial target area(s) for three or more years. The best lines are candidates for new commercial varieties; those still deficient in a few traits may be used as parents to produce new populations for further selection.

These processes, which lead to the final step of marketing and distribution, is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard variety. If a single observation is inconclusive, replicated observations provide a better estimate of its genetic worth.

The goal of watermelon breeding is to develop new and superior watermelon varieties and hybrids. The breeder initially selects and crosses two or more parental lines, followed by repeated selfing and selection, producing many new genetic combinations. The breeder can theoretically generate billions of different genetic combinations via crossing, selection, selfing and mutations.

Using Inbred Watermelon Lines WTL0088, WTL0089, WDL0090 and WTL0091 to Develop Other Watermelon Varieties Watermelon varieties such as inbred watermelon lines WTL0088, WTL0089, WDL0090 or WTL0091 are typically developed for the use as parental lines in the production of triploid hybrids for fresh market consumption. Plant breeding techniques known in the art and used in a watermelon breeding program include, but are not limited to, recurrent selection, mass selection, bulk selection, mass selection, backcrossing, pedigree breeding, open pollination breeding, restriction fragment length polymorphism enhanced selection, genetic marker enhanced selection, making double haploids, transformation, and gene editing. These techniques can be used singularly or in combinations. The development of watermelon varieties in a breeding program requires, in general, the development and evaluation of homozygous varieties. There are many analytical methods available to evaluate a new variety. The oldest and most traditional method of analysis is the observation of phenotypic traits, but genotypic analysis may also be used.

Additional Breeding Methods

One embodiment is directed to methods for producing a watermelon plant by crossing a first parent watermelon plant with a second parent watermelon plant, wherein the first or second watermelon plant is the watermelon plant from inbred watermelon lines WTL0088, WTL0089, WDL0090 or WTL0091. Further, both first and second parent watermelon plants may be from inbred watermelon line WTL0088, WTL0089, WDL0090 or WTL0091. Any plants produced using inbred watermelon line WTL0088, WTL0089, WDL0090 or WTL0091 as at least one parent are also within the scope of the embodiments. These methods are well known in the art and some of the more commonly used breeding methods are described herein. Descriptions of breeding methods can be found in one of several reference books (e.g., Allard, Principles of Plant Breeding (1960); Simmonds, Principles of Crop Improvement (1979); Sneep, et al. (1979); Cooper, S. G., D. S. Douches and E. J. Grafius. 2004.

The following describes breeding methods that may be used with inbred watermelon line WTL0088, WTL0089, WDL0090 or WTL0091 in the development of further watermelon plants, including inbreds or hybrids. One such embodiment is a method for developing an inbred watermelon line WTL0088, WTL0089, WDL0090 or WTL0091 progeny plant in a watermelon breeding program comprising: obtaining the watermelon plant, or a part thereof, of inbred watermelon line WTL0088, WTL0089, WDL0090 or WTL0091, utilizing said plant, or plant part, as a source of breeding material, and selecting an inbred watermelon line WTL0088, WTL0089, WDL0090 or WTL0091 progeny plant with molecular markers in common with inbred watermelon line WTL0088, WTL0089, WDL0090 or WTL0091 and/or with morphological and/or physiological characteristics selected from the characteristics listed in Table 1. Breeding steps that may be used in the watermelon plant breeding program include pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

Another method involves producing a population of inbred watermelon line WTL0088, WTL0089, WDL0090 or WTL0091 progeny watermelon plants, comprising crossing inbred watermelon line WTL0088, WTL0089, WDL0090 or WTL0091 with another watermelon plant, thereby producing a population of watermelon plants which derive 50% of their alleles from inbred watermelon line WTL0088, WTL0089, WDL0090 or WTL0091. A plant of this population may be selected and repeatedly selfed or sibbed with an inbred watermelon line resulting from these successive filial generations. One embodiment is the inbred watermelon line produced by this method and that has obtained at least 50% of its alleles from inbred watermelon lines WTL0088, WTL0089, WDL0090 or WTL0091.

One of ordinary skill in the art of plant breeding would know how to evaluate the traits of two plant varieties to determine if there is no significant difference between the two traits expressed by those varieties. For example, see, Fehr and Walt, Principles of Variety Development, pp. 261-286 (1987). Thus, embodiments include inbred watermelon line WTL0088, WTL0089, WDL0090 or WTL0091 progeny watermelon plants comprising a combination of at least two inbred watermelon line WTL0088, WTL0089, WDL0090 or WTL0091 traits selected from the group consisting of those listed in Table 1 and a combination of traits listed in the Summary, so that said progeny watermelon plant is not significantly different for said traits than inbred watermelon line WTL0088, WTL0089, WDL0090 or WTL0091 as determined at the 5% significance level when grown in the same environmental conditions. Using techniques described herein, molecular markers may be used to identify said progeny plant as an inbred watermelon line WTL0088, WTL0089, WDL0090 or WTL0091 progeny plant. Mean trait values may be used to determine whether trait differences are significant, and preferably the traits are measured on plants grown under the same environmental conditions. Once such a variety is developed, its value is substantial since it is important to advance the germplasm base as a whole in order to maintain or improve traits such as yield, disease tolerance, pest tolerance, and plant performance in extreme environmental conditions.

Progeny of inbred watermelon line WTL0088, WTL0089, WDL0090 or WTL0091 may also be characterized through their filial relationship with inbred watermelon line WTL0088, WTL0089, WDL0090 or WTL0091, as for example, being within a certain number of breeding crosses of inbred watermelon line WTL0088. A breeding cross is a cross made to introduce new genetics into the progeny, and is distinguished from a self or a sib cross, which is made to select among existing genetic alleles. The lower the number of breeding crosses in the pedigree, the closer the relationship between inbred watermelon line WTL0088, WTL0089, WDL0090 or WTL0091 and its progeny. For example, progeny produced by the methods described herein may be within 1, 2, 3, 4, or 5 breeding crosses of inbred watermelon line WTL0088, WTL0089, WDL0090 or WTL0091.

Pedigree Breeding

Pedigree breeding starts with the crossing of two genotypes, such as inbred watermelon line WTL0088, WTL0089, WDL0090 or WTL0091 and another inbred watermelon line having one or more desirable characteristics that is lacking or which complements inbred watermelon line WTL0088, WTL0089, WDL0090 or WTL0091. If the two original parents do not provide all the desired characteristics, other sources can be included in the breeding population. In the pedigree method, superior plants are selfed and selected in successive filial generations. In the succeeding filial generations, the heterozygous condition gives way to homogeneous varieties as a result of self-pollination and selection. Typically, in the pedigree method of breeding, five or more successive filial generations of selfing and selection is practiced: $F_1$ to $F_2$; $F_2$ to $F_3$; $F_3$ to $F_4$; $F_4$ to $F_5$; etc. After a sufficient amount of inbreeding, successive filial generations will serve to increase seed of the developed variety. Preferably, the developed variety comprises homozygous alleles at about 95% or more of its loci.

Backcross Breeding

Backcross breeding has been used to transfer genes for a simply inherited, highly heritable trait into a desirable homozygous variety or inbred line which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have the attributes of the recurrent parent (e.g., variety) and the desirable trait transferred from the donor parent. This is also known as single gene conversion and/or backcross conversion.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, when compared in the same environment, other than an occasional variant trait that might arise during backcrossing or direct introduction of a transgene, and therefore the desired physiological and morphological constitution of the original variety. The choice of the particular nonrecurrent parent will depend on the purpose of the backcross; one of the major purposes is to add some agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance, it may be necessary to introduce a test of the progeny to determine if the desired characteristic has been successfully transferred.

A backcross conversion of inbred watermelon line WTL0088, WTL0089, WDL0090 or WTL0091 occurs when DNA sequences are introduced through backcrossing, with inbred watermelon line WTL0088 utilized as the recurrent parent. Both naturally occurring and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least 5 crosses, and the like. Molecular marker assisted breeding or selection may be utilized to reduce the number of backcrosses necessary to achieve the backcross conversion. For example, see, Frisch M. et al, "Marker-Assisted Backcrossing for Simultaneous Introgression of Two Genes" *Crop Science Society of America*, pp 1716-1725 (2001) and Openshaw, S. J., et al., "Marker-assisted Selection in Backcross Breeding, Proceedings Symposium of the Analysis of Molecular Data" *Crop Science Society of America*, Corvallis, Oreg. (August 1994), where it was demonstrated that a backcross conversion could be made in as few as two backcrosses.

The complexity of the backcross conversion method depends on the type of trait being transferred (single genes or closely linked genes as compared to unlinked genes), the level of expression of the trait, the type of inheritance (cytoplasmic or nuclear), and the types of parents included in the cross. It is understood by those of ordinary skill in the art that for single gene traits that are relatively easy to classify, the backcross method is effective and relatively easy to manage. Desired traits that may be transferred through backcross conversion include, but are not limited to, sterility (nuclear and cytoplasmic), fertility restoration, nutritional enhancements, drought tolerance, nitrogen utilization, low phytate, industrial enhancements, disease tolerance (bacterial, fungal, or viral), insect tolerance, and herbicide tolerance. In addition, an introgression site itself, such as an FRT site, Lox site, or other site-specific integration site, may be inserted by backcrossing and utilized for direct insertion of one or more genes of interest into a specific plant variety. In some embodiments, the number of loci that may be backcrossed into inbred watermelon line WTL0088, WTL0089, WDL0090 or WTL0091 is at least 1, 2, 3, 4, or 5, and/or no more than 6, 5, 4, 3, or 2. A single locus may contain several transgenes, such as a transgene for disease tolerance that, in the same expression vector, also contains a transgene for herbicide tolerance. The gene for herbicide tolerance may be used as a selectable marker and/or as a phenotypic trait. A single locus conversion of site-specific integration system allows for the integration of multiple genes at the converted loci.

The backcross conversion may result from either the transfer of a dominant allele or a recessive allele. Selection of progeny containing the trait of interest is accomplished by direct selection for a trait associated with a dominant allele. Transgenes transferred via backcrossing typically function as a dominant single gene trait and are relatively easy to classify. Selection of progeny for a trait that is transferred via a recessive allele requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Along with selection for the trait of interest, progeny are selected for the phenotype of the recurrent parent. The backcross is a form of inbreeding, and the features of the recurrent parent are automatically recovered after successive backcrosses. Poehlman, "Breeding Field Crops" p. 204 (1987). Poehlman suggests from one to four or more backcrosses, but as noted above, the number of backcrosses necessary can be reduced with the use of molecular markers. Other factors, such as a genetically similar donor parent, may also reduce the number of backcrosses necessary. As noted by Poehlman, backcrossing is easiest for simply inherited, dominant, and easily recognized traits.

One process for adding or modifying a trait or locus in inbred watermelon line WTL0088, WTL0089, WDL0090 or WTL0091 comprises crossing inbred watermelon line WTL0088, WTL0089, WDL0090 or WTL0091 plants grown from inbred watermelon line WTL0088, WTL0089, WDL0090 or WTL0091 seed with plants of another inbred watermelon line that comprise the desired trait or locus, selecting $F_1$ progeny plants that comprise the desired trait or locus to produce selected $F_1$ progeny plants, crossing the selected progeny plants with the inbred watermelon line WTL0088, WTL0089, WDL0090 or WTL0091 plants to produce backcross progeny plants, selecting for backcross progeny plants that have the desired trait or locus and the morphological characteristics of inbred watermelon line WTL0088, WTL0089, WDL0090 or WTL0091 to produce selected backcross progeny plants, and backcrossing to inbred watermelon line WTL0088, WTL0089, WDL0090 or WTL0091 three or more times in succession to produce selected fourth or higher backcross progeny plants that comprise said trait or locus. The modified inbred watermelon line WTL0088, WTL0089, WDL0090 or WTL0091 may be further characterized as having the physiological and morphological characteristics of inbred watermelon line WTL0088, WTL0089, WDL0090 or WTL0091 listed in Table 1 as determined at the 5% significance level when grown in the same environmental conditions and/or may be characterized by percent similarity or identity to inbred watermelon line WTL0088, WTL0089, WDL0090 or WTL0091 as determined by SSR markers. The above method may be utilized with fewer backcrosses in appropriate situations, such as when the donor parent is highly related or markers are used in the selection step. Desired traits that may be used include those nucleic acids known in the art, some of which are listed herein, that will affect traits through nucleic acid expression or inhibition. Desired loci include the introgression of FRT, Lox, and other sites for site specific integration, which may also affect a desired trait if a functional nucleic acid is inserted at the integration site.

In addition, the above process and other similar processes described herein may be used to produce first generation progeny watermelon seed by adding a step at the end of the process that comprises crossing inbred watermelon line WTL0088, WTL0089, WDL0090 or WTL0091 with the introgressed trait or locus with a different watermelon plant and harvesting the resultant first generation progeny watermelon seed.

Many single gene traits have been identified that are not regularly selected for in the development of a new variety but that can be improved by backcrossing techniques well-known in the art. Single gene traits may or may not be transgenic. Examples of these traits include, but are not limited to, herbicide tolerance, insect tolerance, tolerance for bacterial, fungal, or viral disease, male fertility, male sterility, enhanced nutritional quality, modified carbohydrate metabolism, modified yield, modified glycoalkaloid content, and industrial usage In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent, but at the same time retain many components of the nonrecurrent parent by stopping the backcrossing at an early stage and proceeding with selfing and selection. For example, an inbred watermelon line may be crossed with another variety to produce a first-generation progeny plant. The first-generation progeny plant may then be backcrossed to one of its parent varieties to create a $BC_1$ or $BC_2$. Progeny are selfed and selected so that the newly developed variety has many of the attributes of the recurrent parent and yet several of the desired attributes of the nonrecurrent parent. This approach leverages the value and strengths of the recurrent parent for use in new watermelon varieties.

Therefore, an embodiment of the present disclosure is a method of making a backcross conversion inbred watermelon line WTL0088, WTL0089, WDL0090 or WTL0091, comprising the steps of crossing a plant of inbred watermelon line WTL0088, WTL0089, WDL0090 or WTL0091 with a donor plant comprising a desired trait, selecting an $F_1$ progeny plant comprising the desired trait, and backcrossing the selected $F_1$ progeny plant to a plant of inbred watermelon line WTL0088, WTL0089, WDL0090 or WTL0091 to produce $BC_1$, $BC_2$, $BC_3$, etc. This method may further comprise the step of obtaining a molecular marker profile of inbred watermelon line WTL0088, WTL0089, WDL0090 or WTL0091 and using the molecular marker profile to select for a progeny plant with the desired trait and the molecular marker profile of inbred watermelon line WTL0088, WTL0089, WDL0090 or WTL0091. In one embodiment, the desired trait is a mutant gene, gene, or transgene present in the donor parent.

Recurrent Selection and Mass Selection

Recurrent selection is a method used in a plant breeding program to improve a population of plants. Inbred watermelon line WTL0088, WTL0089, WDL0090 or WTL0091 is suitable for use in a recurrent selection program. The method entails individual plants cross pollinating with each other to form progeny. The progeny are grown and the superior progeny selected by any number of selection methods, which include individual plant, half-sib progeny, full-sib progeny, and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic variety. A synthetic variety is the resultant progeny formed by the intercrossing of several selected varieties.

Mass selection is a useful technique when used in conjunction with molecular marker enhanced selection. In mass selection, seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk, and then using a sample of the seed harvested in bulk to plant the next generation. Also, instead of self-pollination, directed pollination could be used as part of the breeding program.

Mass and recurrent selections can be used to improve populations of either self- or cross-pollinating crops. A genetically variable population of heterozygous individuals is either identified, or created, by intercrossing several different parents. The plants are selected based on individual superiority, outstanding progeny, or excellent combining ability. The selected plants are intercrossed to produce a new population in which further cycles of selection are continued.

Mutation Breeding

Mutation breeding is another method of introducing new traits into inbred watermelon line WTL0088, WTL0089, WDL0090 or WTL0091. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil)), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques. Details of mutation breeding can be found in Fehr, "Principles of Variety Development," Macmillan Publishing Company (1993). In addition, mutations created in other watermelon plants may be used to produce a backcross conversion of inbred watermelon line WTL0088, WTL0089, WDL0090 or WTL0091 that comprises such mutation.

Additional methods include, but are not limited to, expression vectors introduced into plant tissues using a direct gene transfer method, such as microprojectile-mediated delivery, DNA injection, electroporation, and the like. More preferably, expression vectors are introduced into plant tissues by using either microprojectile-mediated delivery with a biolistic device or by using *Agrobacterium*-mediated transformation. Transformant plants obtained with the protoplasm of the embodiments are intended to be within the scope of the embodiments.

Gene Editing Using CRISPR

Targeted gene editing can be done using CRISPR/Cas9 technology (Saunders & Joung, *Nature Biotechnology*, 32, 347-355, 2014). CRISPR is a type of genome editing system that stands for Clustered Regularly Interspaced Short Palindromic Repeats. This system and CRISPR-associated (Cas) genes enable organisms, such as select bacteria and archaea, to respond to and eliminate invading genetic material. Ishino, Y., et al. *J. Bacteriol.* 169, 5429-5433 (1987). These repeats were known as early as the 1980s in *E. coli*, but Barrangou and colleagues demonstrated that *S. thermophilus* can acquire resistance against a bacteriophage by integrating a fragment of a genome of an infectious virus into its CRISPR locus. Barrangou, R., et al. *Science* 315, 1709-1712 (2007). Many plants have already been modified using the CRISPR system, including *Capsicum annuum*. See for example, Yildirum, Dr. Kubilay, Ondokuz Mayis University, Department of Molecular Biology, "Genetic Conferring Multiple Resistance to DNA Viruses in Plants with CRISPR/Cas9 Genome Editing Technology", European Cooperation in Science and Technology (2020), U.S. Application Publication No. WO2014068346 (György et al., Identification of a *Xanthomonas euvesicatoria* resistance gene from pepper (*Capsicum annuum*) and method for generating plants with resistance), Martinelli, F. et al., "Proposal of a Genome Editing System for Genetic Resistance to Tomato Spotted Wilt Virus" *American Journal of Applied Sciences* 2014, and Noman, A. et al., "CRISPR-Cas9: Tool for Qualitative and Quantitative Plant Genome Editing" *Frontiers in Plant Science* Vol. 7 Nov. 2016.

Gene editing can also be done using crRNA-guided surveillance systems for gene editing. Additional information about crRNA-guided surveillance complex systems for gene editing can be found in the following documents, which are incorporated by reference in their entirety: U.S. Application Publication No. 2010/0076057 (Sontheimer et al., Target DNA Interference with crRNA); U.S. Application Publication No. 2014/0179006 (Feng, CRISPR-CAS Component Systems, Methods, and Compositions for Sequence Manipulation); U.S. Application Publication No. 2014/0294773 (Brouns et al., Modified Cascade Ribonucleoproteins and Uses Thereof); Sorek et al., *Annu. Rev. Biochem.* 82:273-266, 2013; and Wang, S. et al., *Plant Cell Rep* (2015) 34: 1473-1476.

Therefore, it is another embodiment to use the CRISPR system on inbred watermelon line WTL0088, WTL0089, WDL0090 or WTL0091 to modify traits and resistances or tolerances to pests, herbicides, and viruses.

Introduction of a New Trait or Locus into Inbred Watermelon Line WTL0088, WTL0089, WDL0090 or WTL0091

Inbred watermelon line WTL0088, WTL0089, WDL0090 or WTL0091 represents a new variety into which a new locus or trait may be introgressed. Direct transformation and backcrossing represent two important methods that can be used to accomplish such an introgression. The term backcross conversion and single locus conversion are used interchangeably to designate the product of a backcrossing program.

Molecular Techniques Using Inbred Watermelon Line WTL0088, WTL0089, WDL0090 or WTL0091

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to "alter" (the utilization of up-regulation, down-regulation, or gene silencing) the traits of a plant in a specific manner. Any DNA sequences, whether from a different species or from the same species, which are introduced into the genome using transformation or various breeding methods are referred to herein collectively as "transgenes." In some embodiments, a transgenic variant of inbred watermelon line WTL0088, WTL0089, WDL0090 or WTL0091 may contain at least one transgene. Over the last fifteen to twenty years several methods for producing transgenic plants have been developed, and another embodiment also relates to transgenic variants of the claimed inbred watermelon line WTL0088, WTL0089, WDL0090 or WTL0091.

Nucleic acids or polynucleotides refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine and others can also be used for antisense, dsRNA and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the embodiments may be produced by any means, including genomic preparations, cDNA preparations, in-vitro synthesis, RT-PCR, and in vitro or in vivo transcription.

One embodiment is a process for producing inbred watermelon line WTL0088, WTL0089, WDL0090 or WTL0091 further comprising a desired trait, said process comprising introducing a transgene that confers a desired trait to a watermelon plant of inbred watermelon line WTL0088, WTL0089, WDL0090 or WTL0091. Another embodiment is the product produced by this process. In one embodiment, the desired trait may be one or more of herbicide tolerance, insect tolerance, disease tolerance, or modified carbohydrate metabolism. The specific gene may be any known in the art or listed herein, including: a polynucleotide conferring resistance to imidazolinone, dicamba, sulfonylurea, glyphosate, glufosinate, triazine, PPO-inhibitor herbicides, benzonitrile, cyclohexanedione, phenoxy proprionic acid, and L-phosphinothricin; a polynucleotide encoding a *Bacillus thuringiensis* polypeptide; or a polynucleotide conferring resistance to Tomato spotted wilt virus, *Xanthomonas euvesicatoria*, Bs2, CARAV1, or CaPMEI1.

Numerous methods for plant transformation have been developed, including biological and physical plant transformation protocols. See, for example, Li D. et al, "Establishment of a highly efficient transformation system for pepper (*Capsicum annuum* L.)" *Plant Cell Reports*, pp 785-788 (2003), and Lee Y. H. et al, "A new selection method for pepper transformation: callus-mediated shoot formation" *Plant Cell Reports* pp 50-58 (2004). In addition, expression vectors and in vitro culture methods for plant cell or tissue transformation and regeneration of plants are available. See, for example, Gruber, et al., "Vectors for Plant Transformation," in *Methods in Plant Molecular Biology and Biotechnology*, Glick and Thompson Eds., CRC Press, Inc., Boca Raton, pp. 89-119 (1993) and Nakagawa T. et al, "Development of series of gateway binary vectors, pGWBs, for realizing efficient construction of fusion genes for plant transformation" *Journal of Bioscience and Bioengineering* pp 34-41 (2007).

A genetic trait which has been engineered into the genome of a particular watermelon plant may then be moved into the genome of another variety using traditional breeding techniques that are well known in the plant breeding arts. For example, a backcrossing approach is commonly used to move a transgene from a transformed inbred watermelon line into an already developed inbred watermelon line, and the resulting backcross conversion plant would then comprise the transgene(s).

Various genetic elements can be introduced into the plant genome using transformation. These elements include, but are not limited to, genes, coding sequences, inducible, constitutive and tissue specific promoters, enhancing sequences, and signal and targeting sequences. For example, see the traits, genes, and transformation methods listed in U.S. Pat. No. 6,118,055.

Breeding with Molecular Markers

Molecular markers, which includes markers identified through the use of techniques such as Isozyme Electrophoresis, Restriction Fragment Length Polymorphisms (RFLPs), Randomly Amplified Polymorphic DNAs (RAPDs), Amplified Fragment Length Polymorphisms (AFLPs), Arbitrarily Primed Polymerase Chain Reaction (AP-PCR), DNA Amplification Fingerprinting (DAF), Sequence Characterized Amplified Regions (SCARs), Simple Sequence Repeats (SSRs), and Single Nucleotide Polymorphisms (SNPs) may be used in plant breeding methods utilizing inbred watermelon line WTL0088, WTL0089, WDL0090 or WTL0091.

Isozyme Electrophoresis and RFLPs have been widely used to determine genetic composition. See Richards, Christopher M., et al., "Polymorphic microsatellite markers for inferring diversity in wild and domesticated sugar beet (*Beta vulgaris*), *Molecular Ecology Notes* (2004) 4: Pp. 243-245 and Yudina, Rimma Sergeevna, "Malate dehydrogenase isozymes as markers of the organelles physiological state in sugar beet (*Beta vulgaris* L.)", March 2007, *Sugar Tech*, 9(1):67-71.

Randomly Amplified Polymorphic DNAs (RAPDs) and Amplified Fragment Length Polymorphisms (AFLPs) may also be used. See for example, Izzatullayeva, Vusala, "Efficiency of using RAPD and ISSR markers in evaluation of genetic diversity in sugar watermelon", *Turk. J. Biol.* (2014) 38:429-438 and Grimmer, M. K., et al., "An anchored linkage map for sugar watermelon based on AFLP, SNP and RAPD markers and QTL mapping of a new source of resistance to Watermelon necrotic yellow vein virus" *Theor Appl Genet*. (2007 May) 114(7):1151-60.

SSR technology can be routinely used. See for example, Taški-Ajduković, Ksenija, et al., "Estimation of genetic diversity and relationship in sugar watermelon pollinators based on SSR markers" *J. of Biotechnology* (May 2017) 27: pages: 1-7.

Single Nucleotide Polymorphisms (SNPs) may also be used to identify the unique genetic composition of the embodiment(s) and progeny varieties retaining that unique genetic composition. See for example, Stevanto, Piergiorgio, et al., "High-Throughput RAD-SNP Genotyping for Characterization of Sugar Watermelon Genotypes" *Biotechnology Plant Molecular Biology Reporter* (January 2013) 32(3) and Schneider, K., et al., "Analysis of DNA polymorphisms in sugar beet (*Beta vulgaris* L.) and development of an SNP-based map of expressed genes" *Theor Appl Genet*. (September 2007); 115(5):601-15.

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome. See for example, Gildner, S., et al., "QTL mapping of BNYVV resistance from the WB41 source in sugar beet" *Genome*. (April 2005) 48(2):279-285 and Setiawan, A., et al., "Mapping quantitative trait loci (QTLs) for resistance to *Cercospora* leaf spot disease (*Cercospora beticola* Sacc.) in sugar beet (*Beta vulgaris* L.)", (June 2000) *Theoretical and Applied Genetics* 100(8):1176-1182. QTL markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses.

Expression Vectors for Watermelon Transformation: Marker Genes

Plant transformation involves the construction of an expression vector which will function in plant cells. Such a vector comprises DNA comprising a gene under control of, or operatively linked to, a regulatory element (for example, a promoter). Expression vectors include at least one genetic marker operably linked to a regulatory element (for example, a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well-known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene which, when under the control of plant regulatory signals, confers resistance to kanamycin. Another commonly used selectable marker gene is the hygromycin phosphotransferase gene which confers resistance to the antibiotic hygromycin.

Additional selectable marker genes include Pain1-9a and Pain1-8c which both correspond to the group a alleles of the vacuolar acid invertase gene; Pain1prom-d/e; Stp23-8b, StpL-3b, and StpL-3e which originate from two plastid starch phosphorylase genes; AGPsS-9a which is positively associated with an increase in plant starch content, starch yield and chip quality, and AGPsS-10a which is associated with a decrease in the average plant starch content, starch yield and chip quality; GP171-a which corresponds to allele 1a of ribulose bisphosphate carboxylase activase; and Rca-1a.

Selectable marker genes for plant transformation not of bacterial origin include, for example, mouse dihydrofolate reductase, plant 5-enolpyruvylshikimate-3-phosphate synthase, and plant acetolactate synthase (Eichholtz, et al., *Somatic Cell Mol. Genet.*, 13:67 (1987); Shah, et al., *Science*, 233:478 (1986); Charest, et al., *Plant Cell Rep.*, 8:643 (1990)).

Another class of marker genes for plant transformation requires screening of presumptively transformed plant cells, rather than direct genetic selection of transformed cells, for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used marker genes for screening presumptively transformed cells include β-glucuronidase (GUS), β-galactosidase, luciferase, and chloramphenicol acetyltransferase (Jefferson, R. A., *Plant Mol. Biol. Rep.*, 5:387 (1987); Teeri, et al., *EMBO J.*, 8:343 (1989); Koncz, et al., *Proc. Natl. Acad. Sci. USA*, 84:131 (1987); DeBlock, et al., *EMBO J.*, 3:1681 (1984)).

Expression Vectors for Watermelon Transformation: Promoters

Genes included in expression vectors must be driven by a nucleotide sequence comprising a regulatory element (for example, a promoter). Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in a certain tissue are referred to as "tissue-specific." A "cell-type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell-type specific, and inducible promoters constitute the class of "non-constitutive" promoters. A "constitutive" promoter is a promoter that is active under most environmental conditions. Many types of promoters are well known in the art.

Signal Sequences for Targeting Proteins to Subcellular Compartments

Transport of a protein produced by transgenes to a subcellular compartment, such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine during protein synthesis and processing where the encoded protein is ultimately compartmentalized. Many signal sequences are well-known in the art. See, for example, Becker, et al., *Plant Mol. Biol.*, 20:49 (1992); Knox, C., et al., *Plant Mol. Biol.*, 9:3-17 (1987); Lerner, et al., *Plant Physiol.*, 91:124-129 (1989); Frontes, et al., *Plant Cell*, 3:483-496 (1991); Matsuoka, et al., *Proc. Natl. Acad. Sci.*, 88:834 (1991); Gould, et al., *J. Cell. Biol.*, 108:1657 (1989); Creissen, et al., *Plant J.* 2:129 (1991); Kalderon, et al., *Cell*, 39:499-509 (1984); Steifel, et al., *Plant Cell*, 2:785-793 (1990).

Foreign Protein Genes and Agronomic Genes: Transformation

With transgenic plants according to one embodiment, a foreign protein can be produced in commercial quantities. Thus, techniques for the selection and propagation of transformed plants, which are well understood in the art, yield a plurality of transgenic plants which are harvested in a conventional manner, and a foreign protein can then be extracted from a tissue of interest or from total biomass. Protein extraction from plant biomass can be accomplished by known methods which are discussed, for example, by Heney and Orr, *Anal. Biochem.*, 114:92-6 (1981).

According to an embodiment, the transgenic plant provided for commercial production of foreign protein is a watermelon plant. In another embodiment, the biomass of interest is seed. For the relatively small number of transgenic plants that show higher levels of expression, a genetic map can be generated, primarily via conventional RFLP, PCR, and SSR analysis, which identifies the approximate chromosomal location of the integrated DNA molecule. For exemplary methodologies in this regard, see, Glick and Thompson, *Methods in Plant Molecular Biology and Biotechnology*, CRC Press, Inc., Boca Raton, 269:284 (1993). Map information concerning chromosomal location is useful for proprietary protection of a subject transgenic plant.

Likewise, by means of one embodiment, plants can be genetically engineered to express various phenotypes of agronomic interest. Through the transformation of watermelon, the expression of genes can be altered to enhance disease tolerance, insect tolerance, herbicide tolerance, agronomic, grain quality, and other traits. Transformation can also be used to insert DNA sequences which control or help control male-sterility. DNA sequences native to watermelons, as well as non-native DNA sequences, can be transformed into watermelons and used to alter levels of native or non-native proteins. Various promoters, targeting sequences, enhancing sequences, and other DNA sequences can be inserted into the genome for the purpose of altering the expression of proteins. The interruption or suppression of the expression of a gene at the level of transcription or translation (also known as gene silencing or gene suppression) is desirable for several aspects of genetic engineering in plants.

Many techniques for gene silencing are well-known to one of skill in the art, including, but not limited to, knockouts (such as by insertion of a transposable element such as Mu (Vicki Chandler, *The Maize Handbook*, Ch. 118 (Springer-Verlag 1994)) or other genetic elements such as a FRT, Lox, or other site specific integration sites; antisense technology (see, e.g., Sheehy, et al., *PNAS USA*, 85:8805-8809 (1988) and U.S. Pat. Nos. 5,107,065, 5,453,566, and 5,759,829); co-suppression (e.g., Taylor, *Plant Cell*, 9:1245 (1997); Jorgensen, *Trends Biotech.*, 8(12):340-344 (1990); Flavell, *PNAS USA*, 91:3490-3496 (1994); Finnegan, et al., *Bio/Technology*, 12:883-888 (1994); Neuhuber, et al., *Mol. Gen. Genet.*, 244:230-241 (1994)); RNA interference (Napoli, et al., *Plant Cell*, 2:279-289 (1990); U.S. Pat. No. 5,034,323; Sharp, *Genes Dev.*, 13:139-141 (1999); Zamore, et al., *Cell*, 101:25-33 (2000); Montgomery, et al., *PNAS USA*, 95:15502-15507 (1998)), virus-induced gene silencing (Burton, et al., *Plant Cell*, 12:691-705 (2000); Baulcombe, *Curr. Op. Plant Bio.*, 2:109-113 (1999)); target-RNA-specific ribozymes (Haseloff, et al., *Nature*, 334:585-591 (1988)); hairpin structures (Smith, et al., *Nature*, 407:319-320 (2000); U.S. Pat. Nos. 6,423,885, 7,138,565, 6,753,139, and 7,713,715); MicroRNA (Aukerman & Sakai, *Plant Cell*, 15:2730-2741 (2003)); ribozymes (Steinecke, et al., *EMBO J.*, 11:1525 (1992); Perriman, et al., *Antisense Res. Dev.*, 3:253 (1993)); oligonucleotide mediated targeted modification (e.g., U.S. Pat. Nos. 6,528,700 and 6,911,575); Zn-finger targeted molecules (e.g., U.S. Pat. Nos. 7,151,201, 6,453,242, 6,785,613, 7,177,766 and 7,788,044); and other methods or combinations of the above methods known to those of skill in the art.

The foregoing methods for transformation may be used for producing a transgenic variety. The transgenic variety could then be crossed with another (non-transformed or transformed) variety in order to produce a new transgenic variety. Alternatively, a genetic trait that has been engineered into a particular watermelon line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties that do not contain that gene. As used herein, "crossing" can refer to a simple x by y cross or the process of backcrossing depending on the context.

Likewise, by means of one embodiment, agronomic genes can be expressed in transformed plants. More particularly, plants can be genetically engineered to express various phenotypes of agronomic interest, including, but not limited to, genes that confer resistance or tolerance to pests or disease, genes that confer resistance or tolerance to an herbicide, genes that confer or contribute to a value-added or desired trait, genes that control male sterility, genes that create a site for site specific DNA integration, and genes that affect abiotic stress tolerance. Many hundreds if not thousands of different genes are known and could potentially be introduced into a watermelon plant according to the invention. Non-limiting examples of particular genes and corresponding phenotypes one may choose to introduce into a watermelon plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference in their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety. Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., *Biotech. Gen. Engin. Rev.*, 9:207, 1991). The RNA could also be a catalytic RNA molecule (i.e., a ribozyme) engineered to cleave a desired endogenous mRNA product (see for example, Gibson and Shillito, *Mol. Biotech.*, 7:125, 1997). Thus, any gene which produces a protein or mRNA which expresses a phenotype or morphology change of interest is useful for the practice of one or more embodiments.

Tissue Culture

Further reproduction of the variety can occur by tissue culture and regeneration. Tissue culture of various tissues of watermelons and regeneration of plants therefrom is well-known and widely published. See, for example, Xu, Q. L., et al., "Efficient plant regeneration in vitro from red leaf watermelon via organogenesis", *Russian Journal of Plant Physiology* (2009) 56: 546-550 and Mezei, S., et al., "*Sugar Watermelon Micropropagation*", (April 2014) *Biotechnology & Biotechnological Equipment*. 20(1). Thus, another aspect or embodiment is to provide cells which upon growth and differentiation produce watermelon plants having the physiological and morphological characteristics of inbred watermelon line WTL0088, WTL0089, WDL0090 or WTL0091.

Regeneration refers to the development of a plant from tissue culture. The term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, root, pollen, flowers, seeds, pods, petioles, leaves, stems, roots, root tips, anthers, pistils, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques, the disclosures of which are incorporated herein by reference.

Industrial Uses

Watermelon offers a wide variety of uses in for fresh, processed and cooked fruit. For example, watermelons can be eaten raw or cooked (fried, baked, boiled, etc). Watermelons can also be used to make food coloring, medicine, powders, juices, sweetener, colorings, watermelon pulp, watermelon shreds, raffinate and betaine. Thus, a further embodiment provides for a food product made from a part of the watermelon plant variety WTL0088, WTL0089, WDL0090 or WTL0091.

In addition to the exemplary aspects and embodiments described above, further aspects and embodiments will become apparent by study of the following descriptions.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions, and sub-combinations as are within their true spirit and scope.

One embodiment may be embodied in other specific forms without departing from its spirit or essential characteristics. The described embodiments are to be considered in all respects only as illustrative and not restrictive. All changes which come within the meaning and range of equivalency of the claims are to be embraced within their scope.

Various embodiments, include components, methods, processes, systems and/or apparatus substantially as depicted and described herein, including various embodiments, sub-combinations, and subsets thereof. Those of skill in the art will understand how to make and use an embodiment(s) after understanding the present disclosure.

The foregoing discussion of the embodiments has been presented for purposes of illustration and description. The foregoing is not intended to limit the embodiments to the form or forms disclosed herein. In the foregoing Detailed Description for example, various features of the embodiments are grouped together in one or more embodiments for the purpose of streamlining the disclosure. This method of disclosure is not to be interpreted as reflecting an intention that the embodiment(s) requires more features than are expressly recited in each claim. Rather, as the following claims reflect, inventive aspects lie in less than all features of a single foregoing disclosed embodiment. Thus, the following claims are hereby incorporated into this Detailed Description.

Moreover, though the description of the embodiments has included description of one or more embodiments and certain variations and modifications, other variations and modifications are within the scope of the embodiments (e.g., as may be within the skill and knowledge of those in the art, after understanding the present disclosure). It is intended to obtain rights which include alternative embodiments to the extent permitted, including alternate, interchangeable and/or equivalent structures, functions, ranges or acts to those claimed, whether or not such alternate, interchangeable and/or equivalent structures, functions, ranges or acts are disclosed herein, and without intending to publicly dedicate any patentable subject matter.

The use of the terms "a," "an," and "the," and similar referents in the context of describing the embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the embodiments unless otherwise claimed.

DEPOSIT INFORMATION

A deposit of least 625 seeds of the Sakata Seed America, Inc. proprietary inbred watermelon line WTL0088 disclosed above and recited in the appended claims has been made with the Provasoli-Guillard National Center for Marine Algae and Microbiota, Bigelow Laboratory for Ocean Sciences (NCMA), 60 Bigelow Drive, East Boothbay, Maine 04544. The date of deposit was Mar. 3, 2021. The NCMA No. is 202103002. The deposit of plant tissue was taken from the same deposit maintained by Sakata Seed America, Inc. since prior to the filing date of this application. The deposit will be maintained in the NCMA depository for a period of 30 years, or 5 years after the most recent request, or for the enforceable life of the patent, whichever is longer, and will be replaced if necessary, during that period. Upon issuance, all restrictions on the availability to the public of the deposit will be irrevocably removed consistent with all of the requirements of 37 C.F.R. §§ 1.801-1.809.

A deposit of least 625 seeds of the Sakata Seed America, Inc. proprietary inbred watermelon line WTL0089 disclosed above and recited in the appended claims has been made with the Provasoli-Guillard National Center for Marine Algae and Microbiota, Bigelow Laboratory for Ocean Sciences (NCMA), 60 Bigelow Drive, East Boothbay, Maine 04544. The date of deposit was Mar. 3, 2021. The NCMA No. is 202103003. The deposit of plant tissue was taken from the same deposit maintained by Sakata Seed America, Inc. since prior to the filing date of this application. The deposit will be maintained in the NCMA depository for a period of 30 years, or 5 years after the most recent request, or for the enforceable life of the patent, whichever is longer, and will be replaced if necessary, during that period. Upon issuance, all restrictions on the availability to the public of the deposit will be irrevocably removed consistent with all of the requirements of 37 C.F.R. §§ 1.801-1.809.

A deposit of least 625 seeds of the Sakata Seed America, Inc. proprietary inbred watermelon line WDL0090 disclosed above and recited in the appended claims has been made with the Provasoli-Guillard National Center for Marine Algae and Microbiota, Bigelow Laboratory for Ocean Sciences (NCMA), 60 Bigelow Drive, East Boothbay, Maine 04544. The date of deposit was Mar. 3, 2021. The NCMA No. is 202103004. The deposit of plant tissue was taken from the same deposit maintained by Sakata Seed America, Inc. since prior to the filing date of this application. The deposit will be maintained in the NCMA depository for a period of 30 years, or 5 years after the most recent request, or for the enforceable life of the patent, whichever is longer, and will be replaced if necessary, during that period. Upon issuance, all restrictions on the availability to the public of the deposit will be irrevocably removed consistent with all of the requirements of 37 C.F.R. §§ 1.801-1.809.

A deposit of least 625 seeds of the Sakata Seed America, Inc. proprietary inbred watermelon line WTL0091 disclosed above and recited in the appended claims has been made with the Provasoli-Guillard National Center for Marine Algae and Microbiota, Bigelow Laboratory for Ocean Sciences (NCMA), 60 Bigelow Drive, East Boothbay, Maine 04544. The date of deposit was Mar. 3, 2021. The NCMA No. is 202103005. The deposit of plant tissue was taken from the same deposit maintained by Sakata Seed America, Inc. since prior to the filing date of this application. The deposit will be maintained in the NCMA depository for a period of 30 years, or 5 years after the most recent request, or for the enforceable life of the patent, whichever is longer, and will be replaced if necessary, during that period. Upon issuance, all restrictions on the availability to the public of the deposit will be irrevocably removed consistent with all of the requirements of 37 C.F.R. §§ 1.801-1.809.

What is claimed is:

1. A seed of inbred watermelon line WTL0089, wherein a representative sample of seed of said inbred watermelon line was deposited under NCMA No. 202103003.

2. A watermelon plant, or a part thereof, produced by growing the seed of claim 1.

3. A tissue culture produced from protoplasts or cells from the plant of claim 2, wherein said cells or protoplasts are produced from a plant part selected from the group consisting of leaf, pollen, ovule, embryo, cotyledon, taproot, hypocotyl, meristematic cell, callus, root, root tip, pistil, anther, flower, fruit, seed, shoot, stem, and petiole.

4. A watermelon plant regenerated from the tissue culture of claim 3, wherein said plant has all of the physiological and morphological characteristics of inbred watermelon line WTL0089.

5. A method of producing a progeny watermelon seed, wherein the method comprises crossing the plant of claim 2 with a different watermelon plant and harvesting the resultant watermelon seed.

6. A watermelon seed produced by the method of claim 5.

7. A watermelon plant, produced by growing the seed of claim 6.

8. A method of producing a progeny watermelon seed, wherein the method comprises selfing the plant of claim 2 and harvesting the resultant watermelon seed.

9. A watermelon seed produced by the method of claim 8.

10. A watermelon plant, or a part thereof, produced by growing the seed of claim 9.

11. A method of introducing a desired trait into inbred watermelon line WTL0089, wherein the method comprises: (a) crossing a plant of inbred watermelon line WTL0089, wherein a representative sample of seed was deposited under NCMA No. 202103003, with a plant of another inbred watermelon line that comprises a desired trait to produce progeny plants; (b) selecting one or more progeny plants that have the desired trait; (c) backcrossing the selected progeny plants with inbred watermelon line WTL0089 to produce backcross progeny plants; (d) selecting for backcross progeny plants that have the desired trait; and (e) repeating steps (c) and (d) two or more times in succession to produce selected third or higher backcross progeny plants that comprise the desired trait and all of the physiological and morphological characteristics of inbred watermelon line WTL0089.

12. A watermelon plant produced by the method of claim 11, wherein said plant has the desired trait and otherwise has all of the physiological and morphological characteristics of watermelon WTL0089.

13. The watermelon plant of claim 12, wherein the desired trait is selected from the group consisting of male sterility, herbicide tolerance, insect tolerance, pest tolerance, disease tolerance, environmental stress tolerance, and modified carbohydrate metabolism.

14. A method for producing a seed of a watermelon plant derived from inbred watermelon line WTL0089 comprising the steps of:
(a) crossing the watermelon plant of claim 2 with itself or a second watermelon plant; and
(b) allowing seed to form.

15. The method of claim 14, further comprising the steps of:
(c) growing a plant grown from said seed to yield additional inbred watermelon line WTL0089-derived seed; and
(d) growing said additional inbred watermelon line WTL0089-derived seed of step (c) to yield additional inbred watermelon line WTL0089-derived plants.

16. The method of claim 14, wherein said second watermelon plant is an inbred watermelon plant, wherein said method further comprises:
sowing said seed; and
growing said watermelon seed to yield a hybrid watermelon plant.

17. The method of claim 14, wherein said second watermelon plant is the male inbred watermelon line WDL0090, wherein a representative sample of seed of the inbred watermelon line WDL0090 was deposited under NCMA No. 202103004.

18. The method of claim 17, wherein a hybrid watermelon line XWT8028 is produced.

19. A method of vegetatively propagating a plant of inbred watermelon WTL0089 comprising the steps of:
(a) collecting tissue capable of being propagated from the plant of claim 2;
(b) cultivating said tissue to obtain proliferated shoots; and
(c) rooting said proliferated shoots to obtain rooted plantlets.

20. The method of claim 19, further comprising growing plants from said rooted plantlets.

21. A plant part of the plant of claim 2, wherein the plant part comprises a cell of said inbred watermelon line WTL0089.

22. A method for developing a watermelon plant in a plant breeding program, comprising applying plant breeding techniques to the plant, or plant part thereof, of claim 2, wherein said plant breeding techniques are selected from the group consisting of crossing, recurrent selection, mutation breeding, and wherein said mutation breeding selects for a mutation that is spontaneous or artificially induced, backcrossing, pedigree breeding, marker enhanced selection, haploid/double haploid production, or transformation, wherein application of said techniques results in development of a watermelon plant.

23. A method of introducing a mutation into the genome of inbred watermelon line WTL0089, said method comprising mutagenizing the plant, or plant part thereof, of claim 2, wherein said mutagenizing utilizes temperature, long-term seed storage, tissue culture conditions, ionizing radiation, chemical mutagens, or targeting induced local lesions in genomes, and wherein the resulting plant comprises at least one genome mutation and otherwise has all of the physiological and morphological characteristics of inbred watermelon WTL0089.

24. A method of editing a gene in the genome of inbred watermelon plant of line WTL0089, said method comprises editing the genome of the plant, or plant part thereof, of claim 2, wherein said gene editing utilizes zinc finger nucleases, transcription activator-like effector nucleases (TALENs), engineered homing endonucleases/meganucleases, or the clustered regularly interspaced short palindromic repeat (CRISPR)-associated protein9 (Cas9) system.

25. A watermelon plant produced by the method of claim 24 wherein said plant has the edited gene and otherwise contains all of the morphological and physiological characteristics of inbred watermelon line plant WTL0089.

26. The plant part of claim 2, wherein said plant part is a fruit, a leaf, pollen, an ovule, a cell, a scion, a root, a rootstock, a cutting, or a flower.

* * * * *